United States Patent [19]

Zenkich

[11] Patent Number: 4,687,004
[45] Date of Patent: Aug. 18, 1987

[54] DUAL ELEMENT ELECTRICAL CONNECTOR

[75] Inventor: Ilias R. Zenkich, Norridge, Ill.

[73] Assignee: Zenex Corporation, Chicago, Ill.

[21] Appl. No.: 855,952

[22] Filed: Nov. 30, 1977

Related U.S. Application Data

[63] Continuation-in-part of Ser. No. 754,887, Dec. 27, 1976, abandoned.

[51] Int. Cl.$^4$ .............................................. A61N 1/04
[52] U.S. Cl. .................................. 128/798; 128/803; 128/303.13; 128/419 R; 128/908
[58] Field of Search ............... 128/417, 416, 418, 404, 128/410, 411, 419 R, 303.13, 303.14, 2.06 B, 2.1 R, DIG. 4, 172.1, 2.1 P, 783, 798, 802, 803, 639, 908; 324/51; 361/42

[56] References Cited

U.S. PATENT DOCUMENTS

| | | | |
|---|---|---|---|
| 868,123 | 10/1907 | Randall | 128/418 X |
| 2,590,876 | 4/1952 | Landauer | 128/417 |
| 3,386,445 | 6/1968 | McDonald | 128/417 |
| 3,472,233 | 10/1969 | Sarbacher | 128/417 X |
| 3,601,126 | 8/1971 | Estes | 128/417 X |
| 3,642,008 | 2/1972 | Bolduc | 128/416 |
| 3,817,252 | 6/1974 | Maurer | 128/417 X |
| 3,868,946 | 3/1975 | Hurley | 128/417 X |
| 3,954,100 | 5/1976 | Jacobsen | 128/2.06 E |
| 3,972,329 | 8/1976 | Kaufman | 128/2.06 F |

FOREIGN PATENT DOCUMENTS

| | | | |
|---|---|---|---|
| 1388870 | 10/1971 | Australia | 128/417 |
| 1139927 | 11/1962 | Fed. Rep. of Germany | 128/303.13 |
| 1439302 | 1/1969 | Fed. Rep. of Germany | 128/303.14 |
| 1163803 | 10/1958 | France | 128/418 |

*Primary Examiner*—Lee S. Cohen
*Attorney, Agent, or Firm*—Wood, Dalton, Phillips, Mason & Rowe

[57] ABSTRACT

A dual element electrical connector for body contact has a flexible base with first and second electrodes secured thereto. A cover secured to the base has an aperture which exposes the electrodes. A sponge pad overlies the electrodes and is impregnated with a conductive gel. The cover is secured to the patient, compressing the sponge pad against him for good body contact. A cable and connection circuit couple the first and second electrodes to an electrical treatment apparatus having two terminals each providing or receiving a similar voltage (or ground) to or from the first and second electrodes. The cable and connection circuit are so constructed that if the treatment apparatus is provided with a device to sense the conductivity between the two terminals and the cable becomes disconnected from either the treatment apparatus or the dual element electrical connector, that condition can be detected. The cable is provided with a switch to actuate a test circuit to check the integrity of the electrical circuit from the terminals to the electrodes. The test circuit includes a variable resistor to match the conductivity of the gel with the treatment apparatus.

7 Claims, 5 Drawing Figures

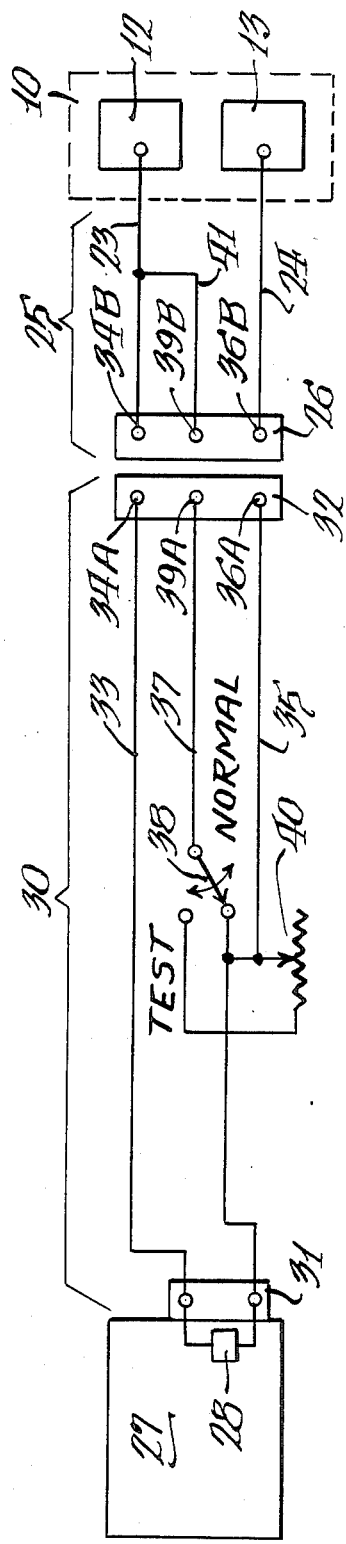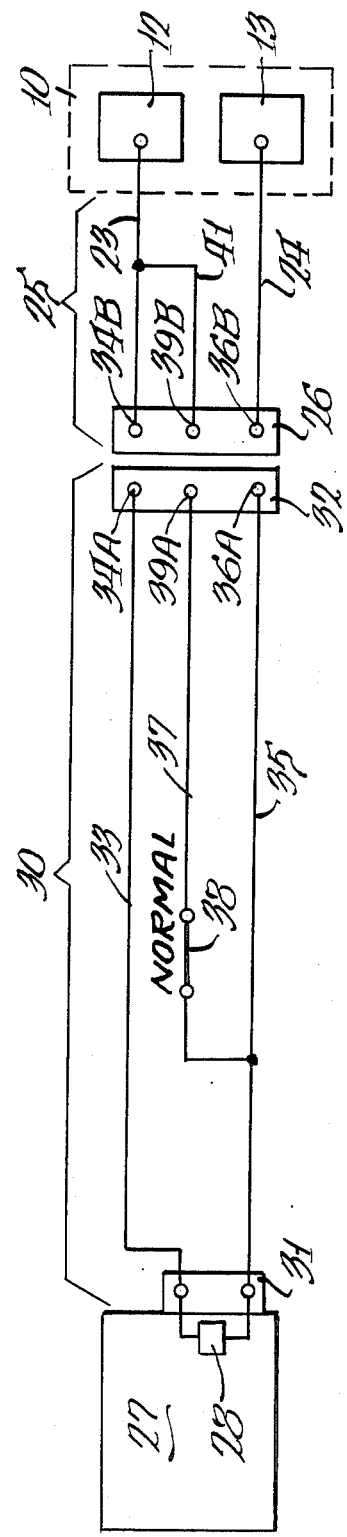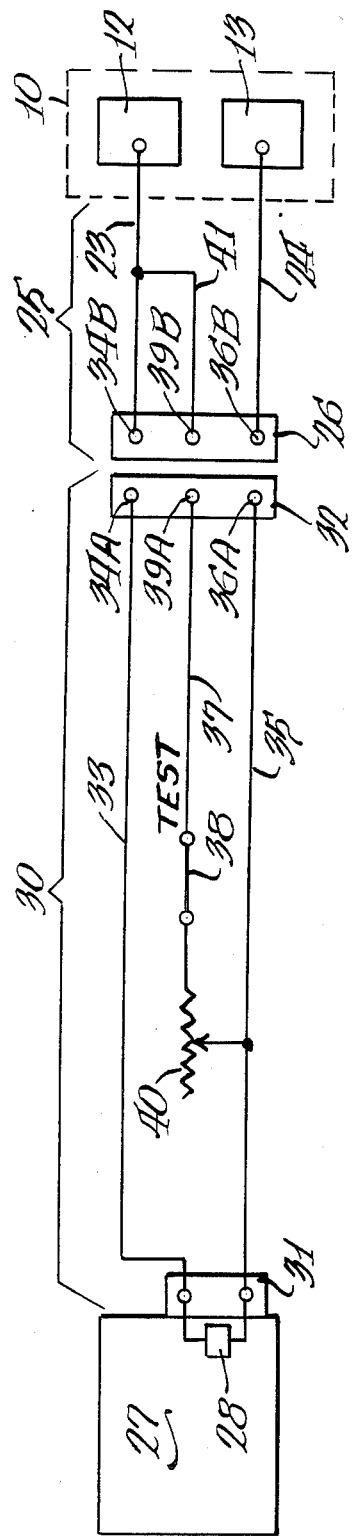

DUAL ELEMENT ELECTRICAL CONNECTOR

RELATED APPLICATION

This application is a continuation-in-part of application Ser. No. 754,887 filed Dec. 27, 1976, now abandoned.

This invention relates to an electrical connector for body contact, a cable and a connection circuit for coupling the electrical connector to an electrical treatment apparatus.

There are medical procedures which require electrical connection to the body of a patient. Many connectors, both reusable and throw-away, have been proposed. This invention is particularly concerned with a throw-away, dual electrode connector which affords reliable connection to the patient's body, and a resuable cable and connection circuit for connecting the dual electrode connector to an electrical treatment apparatus. The construction of the dual element connector, the cable and the connection circuit is simpler, less expensive and more reliable than that of comparable connectors, cables and connection circuits of the prior art, typified by McDonald U.S. Pat. No. 3,386,445 and Bolduc U.S. Pat. No. 3,642,008.

A principal feature of the present invention is the provision of a dual element electrical connector having first and second electrodes secured to the surface of a flexible nonconductive base member. A sponge pad secured to each of the electrodes is impregnated with a conductive gel. A cable and connection circuit couple the electrical treatment apparatus with the electrodes. The cable and connection circuit are constructed such that if they become disconnected from the electrodes or the electrical treatment apparatus, that condition can be detected by the electrical treatment apparatus.

Another feature is that the cable and connection circuit may also include a switch-actuated test circuit for indicating the integrity of the electrical circuit through the cable, the connection circuit, the first and second electrodes, the gel-impregnated sponge pad, and the patient's body.

A further feature is the provision of a variable resistor in the test circuit for matching the conductivity between the first and second electrodes to that desired by the electrical apparatus.

Further features and advantages of the invention will be readily apparent from the following specification and from the drawing in which:

FIG. 3 is a schematic of the cable and the connection circuit coupling the treatment apparatus to the dual element electrical connector;

FIG. 4 is an equivalent schematic diagram of the cable, connection circuit and the dual element electrical connector with an operator-positionable switch in the cable positioned for NORMAL operation; and FIG. 5 is an equivalent schematic diagram of the cable, connection circuit and the dual element electrical connector with the switch in the cable positioned for TEST operation.

Electrical connectors of the general class disclosed herein are used with instruments for detecting and analyzing electrical signals from the body of a patient and with instruments for electrically treating the patient. The dual element connector of this invention is particularly designed and intended for use as a ground connector with an electrical treatment apparatus. It is necessary with such apparatus to have good electrical connection to the patient for effective treatment and to avoid injury. The connector, a cable and a connection circuit provide a reliable connection between the treatment apparatus and the body of the patient.

Figure 1:
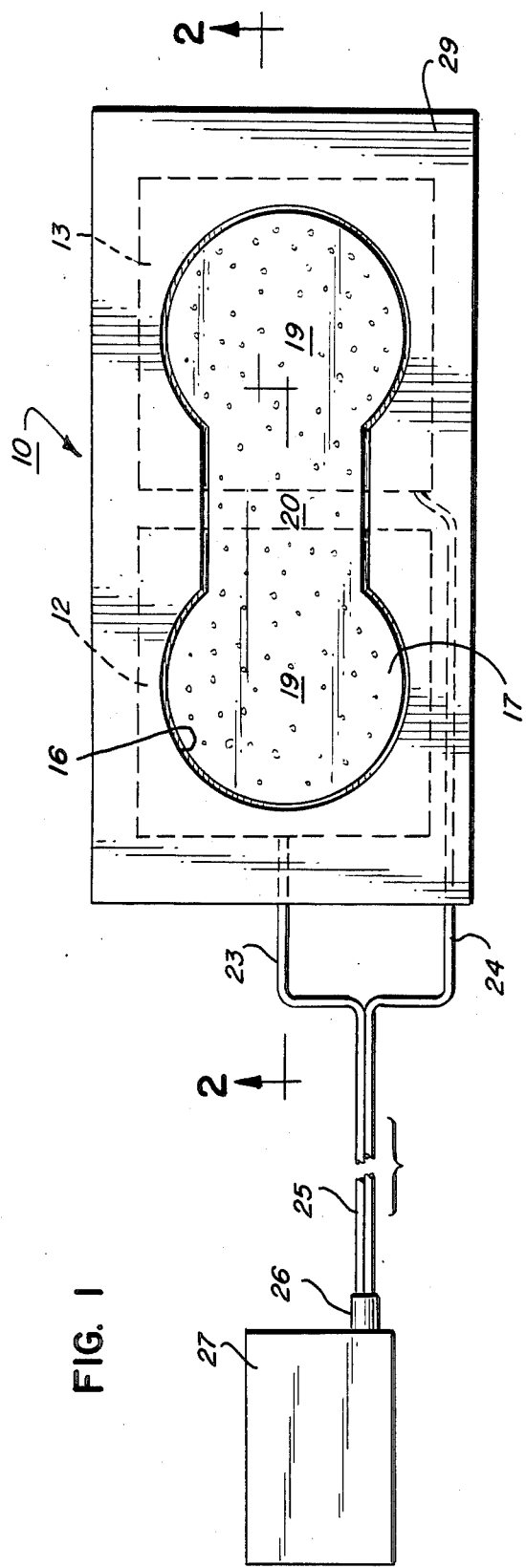
FIG. 1 is a plan view of the dual element electrical connector connected to a diagrammatically illustrated electrical treatment apparatus by the connection circuit.
Figure 2:
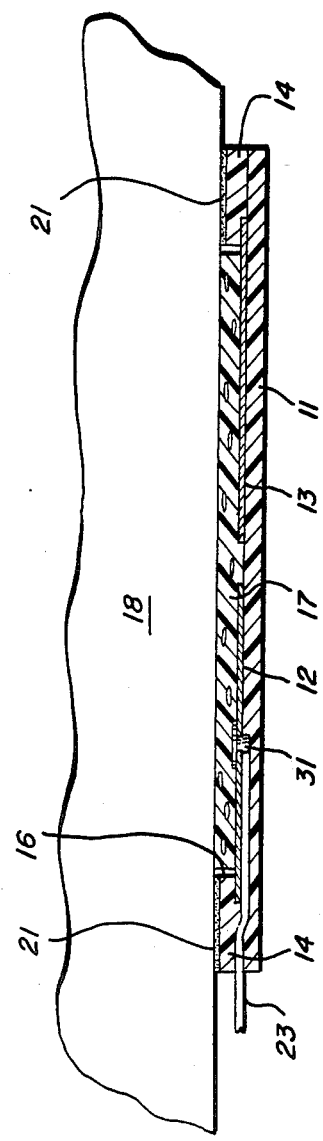
FIG. 2 is a section through the connector taken along the line 2—2 of FIG. 1 and showing application of the connector to a body.

Turning now to FIGS. 1 and 2, the connector 10 has a base 11 of flexible insulating material to which a first and a second spaced-apart electrodes 12 and 13 are secured. A cover 14 of insulating material is secured to base 11 and has an aperture 16 through which both electrodes 12 and 13 are exposed. A sponge pad 17 is located in aperture 16 and engages a principal portion of the surface of each electrode 12 and 13. Sponge pad 17 is impregnated with a conductive gel affording a low resistance path and good electrical connection to the patient's body 18.

Base 11 and cover 14 are preferably of a closed cell plastic foam material which is flexible to conform with the configuration of the patient's body, light in weight, and a satisfactory electrical insulator. Electrodes 12 and 13 may be of aluminum foil, adhesively secured to the surface of base 11. Conductors 23 and 24 are soldered to a connecting stud 15 at the center of each electrode. The male part of a snap fastener is a suitable stud. Pad 17 is preferably an open cell sponge material which may readily be impregnated with the conductive gel affording a low resistance electrical connection between the electrodes 12 and 13 and the patient's body 18 and a reliable electrical interface with the patient's body 18. Preferably, sponge 17 has an uncompressed state extending substantially above the upper surface of cover 14. The cells are open, facilitating impregnation with the conductive gel. Upon application of the connector 10 to the patient's body 18, sponge 17 is compressed, ensuring immediate contact with the surface of the patient's body and reducing the volume of the open cells to minimize the electrical resistance between the electrodes and the patient's body.

Typically, the connector is a one-use or throw-away item which is packaged in a sealed envelope with the sponge pad 17 impregnated with a suitable conductive gel. At the time of use, the connector is removed from the package. Protective sheet 29 is stripped from a coating 21 of a non-irritant adhesive on the surface of cover 14, and the connector is applied to the patient's body. Alternatively, a strap (not shown) may be used in lieu of the adhesive.

Electrical conductors 23 and 24 are connected to jack 26 by electrodes 12 and 13, respectively. Conductors 23 and 24, jack 26 and a jumper wire (not shown) in jack 26 form connection circuit 25. Jack 26 is connected to the electrical treatment apparatus 27. Jack 26 can be directly connected to the electrical treatment apparatus 27 or, alternatively, it may be coupled to a cable (FIG. 3) leading to the electrical treatment apparatus, as will be explained below.

Referring to FIG. 3, cable 30 connects electrical treatment apparatus 27 with connection circuit 25 of dual element connector 10. The cable 30 and connection circuit 25 are constructed so that a disconnection of cable 30 from either the connection circuit 25 or the electrical treatment apparatus 27 can be detected by a sensor 28 which measures the conductivity between the two terminals on the treatment apparatus. The particular sensing device 28 forms no part of the present invention.

Cable 30 includes a two-terminal jack 31 adapted to be received by a similar jack in the electrical treatment apparatus 27 at one end and a three-terminal jack 32 adapted to be received by jack 26 of the connection circuit 25 at the other. The cable 30 may be of any suitable length. A conductor 33 connects one terminal of jack 31 with terminal 34A of jack 32. Another conductor 35 connects the other terminal of jack 31 with terminal 36A of jack 32. A third conductor 37 is coupled between a two-position switch 38 and a third terminal 39A of jack 32.

Jack 26 of connection circuit 25 is provided with a jumper 41 between terminals 34B and 39B. The jumper establishes a current path from conductor 33 to conductor 37 and to switch 38 when jack 26 is properly secured to jack 32 to provide a high conductive condition across sensor 28. When jacks 26 and 32 are improperly mated or are disconnected, there is no current path from conduit 33 to conductor 37. Therefore, a low conductive condition exists across sensor 28.

During operation, switch 38 is positioned to NORMAL and the dual element connector 10 is secured to the body of the patient, as seen in FIG. 4. Return current from the body flows through the conductive gel to pads 12 and 13. Current from conductive pad 12 flows through conductor 23 and jumper 41, terminals 34 and 39 of jacks 26 and 32, conductors 33, 37 and 35 and jack 31 to electrical treatment apparatus 27. Similarly, current from pad 13 flows through conductor 24, terminals 36 of jacks 26 and 32, conductors 35, 37, 41, 23 and 33 and jack 31 to electrical treatment apparatus 27.

The conductivity between the electrodes 12 and 13 may vary depending upon the moisture content of the gel, and whether the dual element connector 10 is connected to the body. The conductivity can be checked by positioning switch 38 in the TEST position. When switch 38 is positioned in the TEST position, variable resistor 40 is connected between conductors 33 and 35 when jack 26 is mated with jack 32. A current path is established from one terminal of the electrical treatment apparatus to the other. Specifically, current flows from one terminal of the electrical treatment apparatus through conductor 33 to conductor 23 and jumper 41 and returns to the other terminal of the electrical treatment apparatus through conductor 37, resistor 40 and conductor 35. An alternate current path is established between electrodes 12 and 13 of dual element connector 10. Thus, resistor 40 is in parallel with the resistance between electrodes 12 and 13 and the conductivity can be measured by sensing device 28. Also, the variable resistor 40 may be set at a value which matches the resistance between the electrodes 12 and 13 to a test circuit in the electrical treatment apparatus 27.

I claim:

1. An improved cable and connection circuit for connecting an electrical treatment apparatus to a dual element electrical connector adapted for a body contact and having a first and second electrode, said electrical treatment apparatus having means for sensing whether the electrical conductivity of said cable and connection circuit is high or low, said cable and connection circuit comprising:
   a cable;
   a connection circuit which includes,
   a first jack having a first, a second and a third terminal,
   a first conductor electrically connected to said first terminal and adapted for electrical connection to said first electrode,
   a second conductor electrically connected to said third terminal and adapted for electrical connection to said second electrode,
   a jumper conductor electrically connected to said first and second terminals; and
   means for connecting the cable to the electrical treatment apparatus and to the connection circuit.

2. The improved cable and connection circuit of claim 1 further including:
   variable resistor means in said cable for matching the conductivity between the first and second electrodes of the dual element electrical connector to a selected conductivity across said sensing means.

3. The improved cable and connection circuit of claim 1 wherein the cable and the means for connecting the cable to the electrical treatment apparatus and to the connection circuit includes:
   a second jack having a first and a second terminal, and adapted to be electrically connected to said treatment apparatus;
   a third jack having a first, a second and a third terminal, and electrically connected to the first, second and third terminals, respectively, of said first jack;
   a third conductor electrically connected to the first terminal of the second jack and to the first terminal of the third jack;
   a fourth conductor electrically connected to the second terminal of the second jack and to the third terminal of the third jack;
   a fifth conductor electrically connected to the second terminal of the third jack and to the conductor connecting the second terminal of the second jack to the third terminal of the third jack.

4. The improved cable and connection circuit of claim 3 further including:
   a two-position switch connected between the fourth and the fifth conductors for electrically connecting said fourth conductor to said fifth conductor in one position and for electrically connecting a variable resistor between the fourth and the fifth conductors in the other position.

5. In an electrical treatment apparatus for detecting or analyzing electrical signals from the body of a patient or for applying electrical signals to the body, an improved cable, connection circuit, and dual element electrical connector for body contact, comprising:
   a dual element electrical connector having
   a base of nonconductive flexible material;
   a first electrode secured to said base;
   a second electrode secured to said base and spaced from said first electrode;
   a cover of flexible nonconductive material having an aperture and secured to said base, said electrodes being exposed through said cover aperture;
   a sponge pad secured to each of said electrodes for body contact; and a conductive gel impregnating said sponge pad;
   a connection circuit having
   a first conductor electrically connected to said first electrode;
   a second conductor electrically connected to said second electrode; and a first jack electrically connected to said first and second conductors;

a cable for electrically connecting the electrical treatment apparatus to the connection circuit having a second jack adapted to be electrically connected to the electrical treatment apparatus;

a third jack mated with said first jack;

conductor means coupled between said second and third jacks for electrically connecting said first and second conductors to said electrical treatment apparatus;

a switch;

means responsive to said switch and coupled through said first and second jacks for providing a short circuit between said first and second conductors when said first jack is mated with said third jack and said switch is in one position; and means responsive to said switch and coupled through said first and second jacks for providing an adjustable resistance between said first and second conductors when said first jack is mated with said third jack and said switch is in another position.

6. The dual element electrical connector of claim 5 in which said sponge pad extends above said cover for engagement with said body.

7. The dual element electrical connector of claim 6 in which said cover has an adhesive coating.

* * * * *